US006028083A

United States Patent [19]
Carr et al.

[11] Patent Number: 6,028,083
[45] Date of Patent: Feb. 22, 2000

[54] ESTERS OF (+)-α-(2,3-DIMETHOXYPHENYL)-1-[2-(4-FLUOROPHENYL) ETHYL]-4-PIPERIDINEMETHANOL

[75] Inventors: Albert A. Carr, Cincinnati, Ohio; Raymond W. Kosley, Jr., Bridgewater, N.J.; Luc Van Hijfte, Wangen, France

[73] Assignee: Hoechst Marion Roussel, Inc., Bridgewater, N.J.

[21] Appl. No.: 08/900,462

[22] Filed: Jul. 25, 1997

[51] Int. Cl.$^7$ ............................ A61K 31/44; C07D 211/34
[52] U.S. Cl. ............................................. 514/317; 546/239
[58] Field of Search .............................. 514/317; 546/239

[56] References Cited

U.S. PATENT DOCUMENTS

| | | | |
|---|---|---|---|
| 2,833,775 | 5/1958 | Sperber et al. | 546/241 |
| 3,058,979 | 10/1962 | Ullyot et al. | 544/45 |
| 3,194,733 | 7/1965 | Yale et al. | 514/225.8 |
| 3,394,131 | 7/1968 | Yale et al. | 544/45 |
| 3,655,676 | 4/1972 | Kaiser et al. | 546/241 |
| 4,569,941 | 2/1986 | Suh et al. | 514/317 |
| 4,623,728 | 11/1986 | Sarges | 546/236 |
| 4,632,929 | 12/1986 | Suh et al. | 514/317 |
| 4,701,461 | 10/1987 | Suh et al. | 514/317 |
| 4,762,842 | 8/1988 | Cohen et al. | 514/288 |
| 4,783,471 | 11/1988 | Carr | 514/317 |
| 4,804,663 | 2/1989 | Kennis et al. | 514/258 |
| 4,810,713 | 3/1989 | Yanni et al. | 514/317 |
| 4,877,798 | 10/1989 | Sorensen | 514/317 |
| 4,895,841 | 1/1990 | Sugimoto et al. | 514/212 |
| 4,908,369 | 3/1990 | Schechter et al. | 514/277 |
| 4,912,117 | 3/1990 | Carr | 514/317 |
| 4,921,863 | 5/1990 | Sugimoto et al. | 514/319 |
| 4,950,614 | 8/1990 | Yanni et al. | 438/74 |
| 4,950,674 | 8/1990 | Yanni et al. | 514/317 |
| 5,021,428 | 6/1991 | Carr | 514/317 |
| 5,064,838 | 11/1991 | Carr et al. | 514/317 |
| 5,070,087 | 12/1991 | Teng et al. | 514/212 |
| 5,100,901 | 3/1992 | Sugimoto et al. | 514/319 |
| 5,106,855 | 4/1992 | McLees et al. | 514/317 |
| 5,112,978 | 5/1992 | Molinari | 546/240 |
| 5,116,846 | 5/1992 | Cain et al. | 514/317 |
| 5,134,149 | 7/1992 | Carr et al. | 514/317 |
| 5,158,952 | 10/1992 | Janssen et al. | 514/258 |
| 5,169,096 | 12/1992 | Carr et al. | 246/232 |
| 5,254,556 | 10/1993 | Janssen et al. | 514/258 |
| 5,561,144 | 10/1996 | Carr et al. | 514/317 |
| 5,618,824 | 4/1997 | Schmidt et al. | 514/317 |
| 5,700,812 | 12/1997 | Carr et al. | 514/317 |
| 5,700,813 | 12/1997 | Carr et al. | 514/317 |
| 5,721,247 | 2/1998 | Carr et al. | 514/307 |

FOREIGN PATENT DOCUMENTS

| | | |
|---|---|---|
| 2982289 | 8/1989 | Australia . |
| 2982389 | 8/1989 | Australia . |
| 0208235 | 1/1987 | European Pat. Off. . |
| 0288563 | 4/1988 | European Pat. Off. . |
| 0296560 | 12/1988 | European Pat. Off. . |
| 0317933 | 5/1989 | European Pat. Off. . |
| 0319962 | 6/1989 | European Pat. Off. . |
| 0337136 | 10/1989 | European Pat. Off. . |
| 0368388 | 5/1990 | European Pat. Off. . |
| 0449186 | 10/1991 | European Pat. Off. . |
| 0579263 | 1/1994 | European Pat. Off. . |
| 0661266 | 7/1995 | European Pat. Off. . |
| 0673927 | 9/1995 | European Pat. Off. . |
| 0742207 | 11/1996 | European Pat. Off. . |
| 6479151 | 3/1989 | Japan . |
| 7-072171 | 8/1995 | Japan . |
| 86004458 | 6/1986 | South Africa . |
| 86004522 | 12/1986 | South Africa . |
| 86004522 | 12/1987 | South Africa . |
| 8604522 | 9/1997 | South Africa . |
| 1316424 | 5/1970 | United Kingdom . |
| 9626196 | 8/1996 | WIPO . |

OTHER PUBLICATIONS

Tetrahedron: Asymmetry, vol. 4, No. 5 (pp. 943–946) (1993), King.

Tetrahedron: Asymmetry, vol. 1, No. 8 (pp. 535–536) (1990), Nieduzak.

Tetrahedron: Asymmetry, vol. 2, No. 2 (pp. 113–122) (1991), Nieduzak.

Nambu, Keiko et al., *Biochemical Pharmacology*, vol. 36, No. 10, pp. 1715–1722, 1987.

Dencker, Svan Jonas et al., Disease Management, *CNS Drugs*, 1996, Nov:6(5)367–381.

Remington's Pharmaceuticals Sciences, "Sustained–release drug delivery systems", pp. 1687–1688, 18th edition–1990.

Biopharmaceutics (1990), vol. 5, pp. 123–130, C.Hansch, et al., "Comprehensive Medicinal Chemistry." Pergamon Press, Oxford XP002105609.

Pharmazeutische Chemie (1982), pp. 14, 15 & 17, E. Schroeder et al. Georg Thieme Verlag, Stuttgart XP002105610.

Deconoate: International Clinical Psychopharmacology, No. 12 (pp. 255–261) (1997).

An electrophysiological investigation of the mechanism of action of the mechanism of action of the 5–ht2 antagonists ritanserin and mdl 28,133a on amphetamine induced slowing of a 1qO dopamine neurons, abstract of presentation at International Congress on Schizophrenic Research present in Tuscon Arizona on April 21–25, 1991, Sorensen.

Psychopharmacology (1989) 98:45–50: L. Ugedo wt al.

Drugs of the Future vol. 14, No. 5, 1989, pp. 489–490, Janssen.

*Pharmacology and Toxicology Supplement 1*, 1990, 5–7, E. Christensson et al.

(List continued on next page.)

*Primary Examiner*—D. Margaret Seaman
*Attorney, Agent, or Firm*—Carolyn D. Moon

[57] ABSTRACT

The present invention is directed to esters of (+)-α-(2,3 Dimethoxyphenyl)-1-[2-(4-fluorophenyl)ethyl]-4-piperidinemethanol, pharmaceutical formulations, methods of making and methods of using these esters. These compounds antagonize the effects of serotonin at the $5HT_{2A}$ receptor and are useful in treating various conditions such as, for example, psychoses such as schizophrenia.

58 Claims, No Drawings

OTHER PUBLICATIONS

*Pharmacology and Toxicology Supplement 1*, 1990, 12–17, B. Gustaffson et al.

*Life Sciences*, vol. 47, pp. 2401–2408, J. Frank Nash.

*The Journal of Pharmacology and Experimental Therapeutics*, vol. 253, No. 3, 1162–1170, Saller.

*Journal of Neurochemistry*, vol. 54, No. 3, 1990, 1062–1066, Nash et al.

*The Journal of Pharmacology and Experimental Therapeutics*, vol. 249, No. 3, 673–679, Goldstein et al.

Psychopharmacology (1989) vol. 99:S18–S27; H. Y. Meltzer.

*The Journal of Pharmacology and Experimental Therapeutics*, vol. 251:238–246, Meltzer et al.

4–Aroylpiperidines and Related Carbinols as Potent and Selective Inhibitors of Serotonin 5–HT2 Receptors with Antipsychotic Potential, Abstract of presentation at International Congress on Schizophrenic Research present in Tuscon Arizona on Apr. 21–25, 1991.

ent
ESTERS OF (+)-α-(2,3-DIMETHOXYPHENYL)-1-[2-(4-FLUOROPHENYL) ETHYL]-4-PIPERIDINEMETHANOL

FIELD OF THE INVENTION

The present invention is directed to novel compounds useful in treating disease states in patients. More specifically, the present invention is directed to esters of (+)-α-(2,3-dimethoxyphenyl)-1-[2-(4-fluorophenyl)ethyl]-4-piperidinemethanol, pharmaceutical formulations, methods of making and methods of using these compounds. These compounds antagonize the effects of serotonin at the $5HT_{2A}$ receptor and are useful in treating various conditions.

BACKGROUND OF THE INVENTION

The compound (+)-α-(2,3-dimethoxyphenyl)-1-[2-(4-fluorophenyl)ethyl]-4-piperidinemethanol, also known as MDL 100,907, is a potent $5HT_{2A}$ receptor antagonist which is being evaluated in the clinic for treatment of schizophrenia. *J. Pharm. Exp. Ther.* 277:968–9881 (1996) incorporated herein by reference. It was described in U.S. Pat. No. 5,134,149, incorporated herein by reference.

MDL 100,907 antagonizes the effects of serotonin at the $5HT_{2A}$ receptor and thus is useful for treating a variety of conditions. However, this compound may also act directly or indirectly act to achieve therapeutic effects other than by its $5HT_{2A}$ antagonism. For example, see *European Journal of Pharmacology* 273: 273–279 (1995) where MDL 100,907 has been shown to exert a tonic inhibitory influence on dopamine efflux in the medial prefrontal cortex.

An object of the present invention is to provide a new compound which after administration, releases a therapeutically effective amount of MDL 100,907 over an extended period of time. The extended period of time means a time longer than a single dose of MDL 100,907, and would last for several days, several weeks, about one month up to about 6 to about 8 weeks, and preferably from about 2 weeks to about one month.

There are many advantages to administering a single dose of a compound to a patient which lasts over an extended period of time. It can avoid compliance problems which can be particularly important in patients suffering from psychoses or addictive behaviors such as schizophrenia, obsessive compulsive behavior, depression, anxiety, anorexia and drug addiction. Other advantages include an absence of the typical oscillations of drug level achieved with multiple dose therapy through which the patient should experience an improved efficacy in treatment with lower peak drug concentrations.

While the concept of sustained release formulations is not new, not all compounds are capable of being chemically altered to produce a new compound capable of being metabolized into the active ingredient at a desirable rate and over the desired length of time. Other factors contribute to the difficulty of preparing a sustained release formulation such as protein binding and other physiological processes which can affect the therapeutic effect of the active ingredient, see for example *Biochemical Pharmacology*, Vol. 36, No. 10 pp1715–1722 (1987), incorporated herein by reference. Also, the chemically altered compound must be compatible with pharmaceutically acceptable carriers and be stable enough not to substantially degrade on the shelf to the active ingredient. In short, the design of an acceptable sustained release formulation is a difficult, unpredictable task.

SUMMARY OF THE INVENTION

The present invention is a compound of Formula I:

FORMULA I

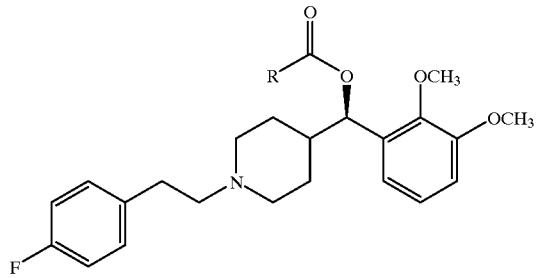

wherein R is $C_1$–$C_{20}$ alkyl, or a stereoisomer or a pharmaceutically acceptable salt thereof. The present invention also comprises:

a pharmaceutical composition comprising the compound of formula I and a pharmaceutically acceptable carrier;

a method of antagonizing the effects of serotonin at the $5HT_{2A}$ receptor comprising administering a compound of formula I to a patient in need thereof;

a method of treating a patient for a disease state comprising administering to the patient in need of such therapy a therapeutically effective amount of a compound of formula I wherein the disease state is psychoses (including schizophrenia), obsessive compulsive disorder, thrombotic illness, coronary vasospasm, depression, anxiety, anorexia nervosa, Raynaud's phenomenon, fibromyalgia, extra-pyramidal side effects, anxiety, arrhythmia, depression, and bipolar depression, or drug abuse; and a method of making the compounds comprising reacting alcohol of structure (5) shown hereafter with an acid halide, acid anhydride or carboxylic acid in the presence of a sufficient amount of an appropriate base.

DETAILED DESCRIPTION OF THE INVENTION

Terms used herein have the following meanings:

a) "Pharmaceutically acceptable salts" means either an acid addition salt or a basic addition salt whichever is possible to make with the compounds of the present invention.

"Pharmaceutically acceptable acid addition salt" is any non-toxic organic or inorganic acid addition salt of the base compounds represented by Formula I. Illustrative inorganic acids which form suitable salts include hydrochloric, hydrobromic, sulfuric and phosphoric acid and acid metal salts such as sodium monohydrogen orthophosphate and potassium hydrogen sulfate. Illustrative organic acids which form suitable salts include the mono-, di- and tri-carboxylic acids. Illustrative of such acids are, for example, acetic, glycolic, lactic, pyruvic, malonic, succinic, glutaric, fumaric, malic, tartaric, citric, ascorbic, maleic, hydroxymaleic, benzoic, hydroxybenzoic, phenylacetic, cinnamic, salicyclic, 2-phenoxybenzoic, p-toluenesulfonic acid and sulfonic acids such is methanesulfonic acid and 2-hydroxyethanesulfonic acid. Either the mono- or di-acid salts can be formed, and such salts can exist in either a hydrated or substantially anhydrous form. In general, the acid addition salts of these compounds are more soluble in water and various hydrophilic organic solvents and which in comparison to their free base forms, generally demonstrate higher melting points.

"Pharmaceutically acceptable basic addition salts" means non-toxic organic or inorganic basic addition salts of the compounds of Formula (I) or any of its intermediates. Examples are alkali metal or alkaline-earth metal hydroxides such as sodium, potassium, calcium, magnesium or barium hydroxides; ammonia, and aliphatic, alicyclic, or aromatic organic amines such as methylamine, trimethylamine and picoline. The selection of the appropriate salt may be important so that the ester is not hydrolyzed. The selection criteria for the appropriate salt will be known to one skilled in the art.

b) "Stereoisomers" is a general term for all isomers of the individual molecules that differ only in the orientation of their atoms in space It includes mirror image isomers (enantiomers), geometric (cis/trans) isomers, and isomers of compounds with more than one chiral center that are not mirror images of one another (diastereoisomers).

c) "Alkyl" means a branched or straight chain alkyl group specified by the amount of carbons in the alkyl group, e.g., C1–C20 alkyl means a one, two, three, four, five, six, seven, eight, nine, ten, eleven, twelve, thirteen, fourteen, fifteen, sixteen, seventeen, eighteen, nineteen, or twenty carbon branched or straight chain alkyl or any ranges thereof, for example, but not limited to C5–C20, C1–C15, C3–C15, C5–C15, C7–C15, and C7–C9.

d) "Patient" means a warm blooded animal, such as for example rat, mice, dogs, cats, guinea pigs, and primates such as humans.

e) "Treat" or "treating" means to alleviate symptoms, eliminate the causation of the symptoms either on a temporary or permanent basis, or to prevent or slow the appearance of symptoms of the named disorder or condition.

f) "Therapeutically effective amount" means an amount of the compound which is effective in treating the named disorder or condition.

g) "Pharmaceutically acceptable carrier" is a non-toxic solvent, dispersant, excipient, adjuvant or other material which is mixed with the compound of the present invention in order to permit the formation of a pharmaceutical composition, i.e., a dosage form capable of administration to the patient. One example of such a carrier is a pharmaceutically acceptable oil typically used for parenteral administration.

The (+)-isomer of α-(2,3-dimethoxyphenyl)-1-[2-(4-fluorophenyl)ethyl]-4-piperidinemethanol can be prepared by methods described in U.S. Pat. No. 5,134,149. One suitable method follows.

SCHEME I
Starting Materials

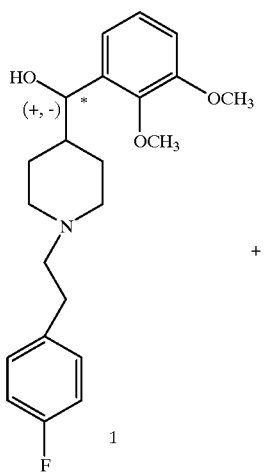

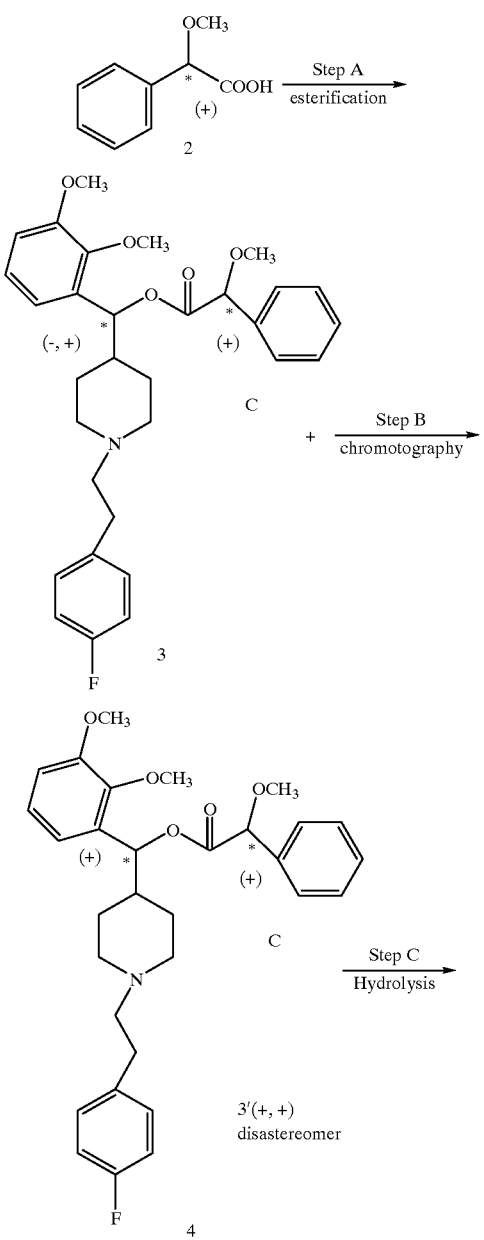

In Step A of Reaction Scheme I, an esterification reaction is carried out between racemic alpha-(2,3-dimethoxyphenyl)-1-[2-(4-fluorophenyl)ethyl]-4-piperidinemethanol (structure 1) and the (+)-isomer of alphamethoxyphenylacetic acid (structure 2). This esterification produces the diastereomeric mixture identified as structure 3. These diastereomers are subjected to silica gel chromatography which separates the two diastereomers, thereby isolating the (+,+) diastereomer as is depicted in Step B. In Step C, the (+,+) diastereomer is hydrolyzed which produces the (+)-isomer of alpha(2,3-dimethoxyphenyl)-1-[2-(4-fluorophenyl)ethyl]-4-piperidinemethanol.

The esterification reaction can be carried out using techniques known in the art.

Typically approximately equivalent amounts of racemic alpha-(2,3-dimethoxyphenyl)-1-[2-(4-fluorophenyl)ethyl]-4-piperidinemethanol and the (+)-isomer of alpha-methoxyphenylacetic is acid are contacted in an organic solvent such as methylene chloride, THF, chloroform, or toluene and heated to reflux for a period of time ranging from 5 to 24 hours. The esterification is typically carried out in the presence of an equivalent amount of dicyclohexylcarbodiimide (DCC) and a catalytic amount of 4-dimethylaminopyridine (DMAP). The resulting diastereomers can be isolated by filtration of the dicyclohexylurea and evaporation of the filtrate.

The diastereomers are then subjected to silica gel chromatography which separates the (+,+) and the (−,+) diastereomers. This chromatographic separation may be carried out as is known in the art. A 1:1 mixture of hexane and ethyl acetate is one suitable eluent.

The resulting (+,+) diastereomer is than subjected to a hydrolysis reaction which produces the (+)-enantiomer of alpha-(2,3-dimethoxyphenyl)-1-[2-(4-fluorophenyl)ethyl]-4-piperidinemethanol. The hydrolysis is carried out by contacting the diastereomer with an excess of a base such as potassium carbonate in an aqueous alcoholic solution. The hydrolysis is carried out at a temperature of about 15 to 30° C. for a period of time ranging from 2 to 24 hours. The resulting (+)-isomer of alpha-(2,3-dimethoxyphenyl)-1-[2-(4-fluorophenyl)ethyl]-4-piperidinemethanol may then be recovered by dilution with water and extraction with methylene chloride. It is then purified by recrystallization from a solvent system such as cyclohexane/hexane or ethyl acetate/hexane.

Methods for producing the starting materials of Reaction Scheme I are known in the s art. For example, U.S. Pat. No. 4,783,471 teaches how to prepare racemic alpha-(2,3-dimethoxyphenyl)-1-[2-(4-fluorophenyl)ethyl]-4-piperidinemethanol. This patent is hereby incorporated by reference. Examples No. 1 and 2 of this application also teach suitable methods. Alternatively, racemic alpha-(2,3-dimethoxyphenyl)-1-[2-(4-fluorophenyl)ethyl]-4-piperidinemethanol can be prepared in the following manner. Initially 4-hydroxypiperidine is io subjected to an N-alkylation reaction with p-fluorophenylethyl bromide which produces 4-hydroxy-1-[2-(4-fluorophenyl)]-piperidine. This compound is brominated with Ph$_3$P.Br$_2$ which produces 4-bromo-1-[2-(4-fluorophenyl)ethyl] piperidine. This compound is contacted with Mg thereby forming a Grignard Reagent which is then reacted with 2,3-dimethoxybenzaldehyde which produces the desired product (±)-alpha-(2,3-dimethoxyphenyl)-1-[2-(4-fluorophenyl)ethyl]-4-piperidinemethanol. The (+)-isomer of alphamethoxyphenylacetic acid is known in the art.

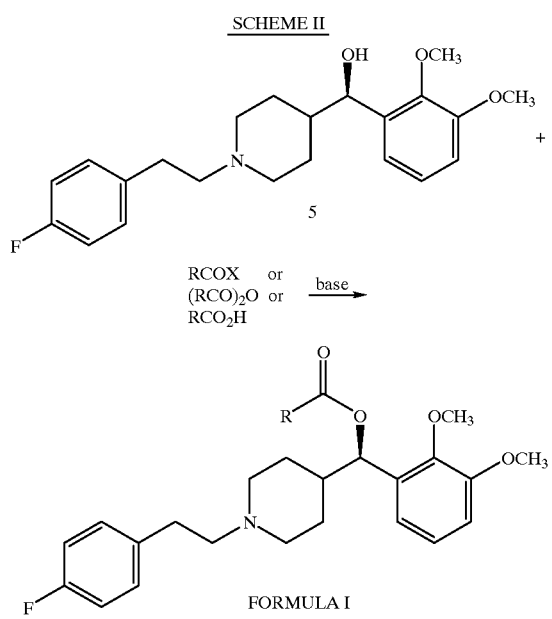

SCHEME II

FORMULA I

Referring to Scheme II, X is chloro or bromo, with chloro being preferred and R is as previously defined. This reaction scheme shows the making of the sustained release compounds of Formula I from the alcohol (5).

The alcohol (5) is reacted with an acid halide (RC(O)X), RCO$_2$H or acid anhydride (RCO)$_2$0 in the presence of an a sufficient amount of an appropriate base. An appropriate base is one that permits ester formation from the acid halide or anhydride. Examples of appropriate bases are trialkylamines, pyridine such as dimethylamino pyridine, diisopropyl ethyl amines, N-methyl morpholines, with triethylamine being preferred. A sufficient amount of the base can be ascertained by one skilled in the art which permits the formation of the compounds of Formula I.

Preferably the base is added to the alcohol (5) and that mixture added dropwise to the acid halide or acid anhydride in an appropriate solvent. Examples of appropriate solvents are chloroform, methylene chloride, or toluene, all of which are readily available, with chloroform being preferred.

The temperature of the reaction may be at a range of about 0–25° C. The reaction mixture may be stirred for from a few hours lo overnight to enhance the reaction. Catalysts may also be added for enhancement of reaction times, e.g., 4-dimethylaminopyridine or the like.

The starting materials for the acid halide (RCOX) are readily available for those skilled in the art. For example, Aldrich Chemical company provides stearoyl chloride, heptadecanoyl chloride, palmitoyl chloride, myristoyl chloride, acetyl chloride, propionyl bromide, propionyl chloride, isovaleryl chloride, valeryl chloride, hexanoyl chloride, hexanoyl chloride, heptanoyl chloride, octanoyl chloride, nonanoyl chloride, decanoyl chloride, undecanoyl chloride and lauroyl chloride. For those acid halides not readily available, one skilled in the art may prepare the acid halide desired. For example, a carboxylic acid may be mixed with a halide donor to produce the desired acid halide. One example of this is to mix carboxylic acid (0.17 mol), methylene chloride (660 mL) and dimethylformamide (0.5 mL) under a nitrogen atmosphere. Add oxalyl chloride (0.2 mol) over about 5 minutes with stirring. Stir at ambient temperature for 3 hours and evaporate the solvent in vacuo to the acid chloride. Another method is to dissolve the carboxylic acid (10 mmol) in methylene chloride (50 mL). Cool to 0° C., place under a nitrogen atmosphere and add, by dropwise addition, thionyl chloride (11 mmol). Stir at room temperature for several hours and evaporate the volatiles in vacuo to give the acid chloride. The carboxylic acids are readily available or can be easily made by those skilled in the art.

The starting materials for the acid anhydrides $(RCO)_2O$ are readily available for those skilled in the art. For example, Aldrich Chemical company provides propionic anhydride, acetic anhydride, butryic anhydride, isobutyric anhydride, valeric anhydride, 2-2,dimethylglutaric anhydride, and phthalic anhydride. Alternatively, acid anhydrides may be synthesized by methods well known in the art.

The starting materials for the acids $(RCO_2H)$ are readily available or may be synthesized by methods well know in the art. For example, see *Advanced Organic Chemistry, Reactions, Mechanisms, and Structure,* 4th ed., John Wiley & Sons, New York 1992, incorporated herein by reference. Aldrich Chemical Company also provides acetic acid, propionic acid, butyric acid, isobutyric acid, isovaleric acid, valeric acid, tert-butylacetic acid, 2,2dimethylbutyric acid, 2-ethylbutyric acid, hexanoic acid, 3-methylvaleric acid, 4-methylvaleric acid, heptanoic acid, octanoic acid, 2-propylpentanoic acid, nanoic acid, decanoic acid, undecanoic acid, lauric acid, tridecanoic acid, myristoleic acid, myristic acid, pentadecanoic acid, palmitic acid, heptadecanoic acid, stearic acid, nonadecanoic acid, eicosanoic acid, as well as others wherein R is between one and twenty alkyl groups.

The following examples are being present to further illustrate the invention. However, they should not be construed as limiting the invention in any manner.

EXAMPLE 1

Starting Material

Example 1, Steps A–D, demonstrates the preparation of the starting material (±)-alpha(2,3-dimethoxyphenyl)-1-[2-(4-fluorophenyl)ethyl]-4-piperidinemethanol, structure 1, Scheme I.

A) 1-[2-(4-Fluorophenyl)ethyl]-4-piperidinecarboxamide

A solution of isonipecotamide (10.9 g, 85.0 mmol), 2-(4-fluorophenyl)ethyl bromide (15.7 g, 77.3 mmol), and $K_2CO_3$ (2.3 g, 167 mmol) was prepared in DMF (280 mL) and stirred under argon at 90–95° C. overnight. The cooled solution was concentrated to a white oily solid. The solid was partitioned between water and $CH_2Cl_2$. The layers were separated and the aqueous layer was extracted with $CH_2Cl_2$. The combined organic layers were washed 2× with water, dried ($MgSO_4$), filtered, and evaporated to a oily solid. The solid was recrystallized from EtOAc to afford 1-[2-(4-fluorophenyl)ethyl]-4-piperidinecarboxamide as a white powder, m.p. 177–178° C. (decomp.). Anal. Calcd for $C_{14}H_{19}FN_2O$: C, 67.18; H, 7.65; N, 11.19. Found: C, 67.25; H, 7.67; N, 11.13.

B) 4-Cyano-1-[2-(4-fluorophenyl)ethyl]piperidine

To stirred phosphorus oxychloride (25 mL, 41.12 g, 268 mmol) and sodium chloride (5.1 g, 87.3 mmol) was added 1-[2-(4-fluorophenyl)ethyl]-4-piperidinecarboxamide (8.9 g, 35.6 mmol) portionwise. After complete addition, the solution was refluxed for 2 hours. The cooled solution was carefully poured into dilute $NH_4OH$ to destroy the $POCl_3$. The aqueous solution was cooled to 0° C., then extracted 2× with $CH_2Cl_2$. The combined organic layers were dried (MgSO), filtered, and evaporated to afford 8.1 g of an oily solid. The solid was distilled, (b.p. 150° C., 0.1 mm Hg), to afford a clear, colorless oil that solidified. This material was crystallized from hexane to afford 4-cyano-1-[2-(4-fluorophenyl)ethyl]piperidine as white needles, m.p. 47–48° C. Anal. Calcd for $C_{14}H_{17}FN_2$: C, 72.39; H, 7.38; N, 12.06. Found: C, 72.62; H, 7.49; N, 12.12.

C) 1-[2-(4-Fluorophenyl)ethyl]-4-piperidinecarboxaldehyde

To a stirred solution of 4-cyano-1-[2-(4-fluorophenyl)-ethyl]piperidine (1.00 g, 4.3 mmol) in THF (20 mL) under argon at 0° C. was added DIBAL-H (4.6 mL of a 1.0 M solution in THF, 4.6 mmol) via syringe. After stirring overnight at room temperature, 10% aqueous HCl (25 mL) was added and the solution was stirred for 3 hours. The entire mixture was then poured into 10% aqueous NaOH (50 mL), then extracted 2× with ether. The combined organic layers were washed with brine, dried ($MgSO_4$), filtered, and evaporated to afford a pale yellow oil. The oil was chromatographed on silica gel, eluting with EtOAc. The appropriate fractions were combined and evaporated to afford an oil. This oil was distilled (b.p. 166° C., 0.05 mm Hg) to afford 1-[2-(4-fluorophenyl)ethyl]-4-piperidinecarboxaldehyde, obtained as a colorless oil. Anal. Calcd for $C_{14}H_{18}FNO$: C, 71.46; H, 7.71; N, 5.95. Found: C, 71.08, H, 7.81; N, 5.86.

D) (±)-alpha(2,3-Dimethoxyphenyl)-1-[2-(4-fluorophenyl)ethyl]-4-piperidinemethanol To a stirred solution of veratrole (0.93 g, 6.7 mmol) in THF (20 mL) under argon at 0° C. was added n-BuLi (2.7 mL of a 2.5 M solution ii hexane, 6.75 mmol). After stirring 2.5 h, the solution was cooled to −78° C. and treated with 1-[2-(4-fluorophenyl)ethyl]-4-piperidinecarboxaldehyde (1.30 g, 5.5 mmol) in THF (25 mL) via an addition funnel. The cooling bath was removed and the solution was allowed to stir for 2 hours. Water was added, the layers separated, and the aqueous layer was extracted with EtOAc. The combined organic layers were washed with brine, dried ($MgSO_4$), filtered, and chromatographed on silica gel, eluting with acetone. The appropriate fractions were combined and evaporated to afford a white solid. The solid was recrystallized from hexane to afford racemic alpha(2,3-dimethoxyphenyl)-1-[2-(4-fluorophenyl)ethyl]-4-piperidinemethanol as shiny white needles, m.p. 126–127° C.

Anal. Calcd for $C_{22}H_{28}FNO_3$: C, 70.75; H, 7.56; N, 3.75. Found: C, 70.87; H, 7.65; N, 3.68.

EXAMPLE 2

Starting Material

Example 2, Steps A–F, demonstrate an alternative manner of preparing (±)-alpha(2,3-dimethoxyphenyl)-1-[2-(4-fluorophenyl)-ethyl]-4-piperidinemethanol, structure 1.

A) 1-(1,1-Dimethylethyl)-1,4-piperidinedicarboxylic acid

To isonipecotic acid (107.5 g, 832 mmol) stirred in 1N NaOH (40 g NaOH in 900 mL $H_2O$) and tert-butanol (1800 mL) was added di-tert-butyl dicarbonate (200 g, 916 mmol) in portions. After stirring overnight, the solution was concentrated and the resulting water layer was acidified with aqueous HCl. This acidic aqueous layer was extracted 3× with ether. The combined organic layers were washed with water, brine, dried ($MgSO_4$), filtered, and evaporated to a white solid, which was recrystallized from EtOAc/hexane (300 mL/200 mL) to afford 1-(1,1-dimethylethyl)-1,4-piperidinedicarboxylic acid as white needles, m.p. 147–149° C.

B) 4-(N-Methoxy-N-methylcarboxamido)-1-piperidinecarboxylic acid 1,1-dimethylethyl ester To a stirred solution of 1-(1,1-dimethylethyl)1,4-piperidinedicarboxylic acid (50.0 g, 218 mmol) in anhydrous $CH_2Cl_2$ (500 mL) under $N_2$ in a 2L flask was added 1,1'-carbonyldiimidazole (38.9 g, 240 mmol) portionwise. After stirring for 1 hour, N,O-dimethylhydroxylamine hydrochloride (23.4 g, 240 mmol) was added in one portion. After stirring overnight, the solution was washed twice with 1N HCl, twice with saturated NaHCO$_3$, once with brine, dried (MgSO$_4$), filtered, and evaporated to an oil. Distillation afforded 4-(N-methoxy-N-methylcarboxamido)-1-piperidinecarboxylic acid 1,1-dimethylethyl ester as a clear oil, b.p. 120–140° C., 0.8 mm.

C) 4-(2,3-Dimethoxybenzoyl)-1-piperidinecarboxylic acid 1,1-dimethylethyl ester n-Butyl lithium (14.5 mL of a 2.5 M solution in hexane, 36.3 mmol) was added via syringe to a stirred solution of veratrole (5.00 g, 36.2 mmol) in THF (50 mL, anhydrous) under argon at 0° C. The ice bath was removed and the mixture was allowed to stir for 90 minutes. The mixture was cooled to −78° C. and treated with 4-(N-methoxy-N-methylcarboxamido)-1-piperidinecarboxylic acid 1,1-dimethylethyl ester (9.20 g, 33.8 mmol) in THF (50 mL, anhydrous) via syringe. The cooling dry ice-acetone bath was removed and the mixture was allowed to come to room temperature. After stirring for 3 hours, saturated aqueous NH$_4$Cl was added and the mixture was allowed to stir overnight. The layers were separated and the aqueous layer was extracted with ether. The combined organic layers were washed with brine, dried (MgSO$_4$), filtered, and evaporated to afford an amber oil. The oil was chromatographed on silica gel, eluting with 20% EtOAc in he:(ane. The appropriate fractions were combined and evaporated to an amber oil. The oil was distilled to afford 4-(2,3-dimethoxybenzoyl)-1-piperidinecarboxylic acid 1,1-dimethylethyl ester as a colorless oil.(b.p. 225–250° C., 0.05 mm). Anal. Calcd for C$_{19}$H$_{27}$NO$_5$: C, 65.31; H, 7.79; N, 4.01. Found: C, 65.04; H, 7.92; N, 4.11.

D) 4-(2,3-Dimethoxyphenyl)-4-piperidinylmethanone 4-(2,3-Dimethoxybenzoyl)-1-piperidinecarboxylic acid 1,1-dimethylethyl ester (7.75 g, 22.2 mmol) was dissolved in trifluoroacetic acid (50 mL, 650 mmol) and stirred for 45 minutes. The entire solution was poured into ether (900 mL) and allowed to stand overnight. Filtration yielded 4-(2,3-dimethoxyphenyl)-4-piperidinylmethanone trifluoroacetate as fine white needles, m.p. 123° C. Anal. Calcd for C$_{14}$H$_{19}$NO$_3$·CF$_3$CO$_2$H: C, 52.89; H, 5.55; N, 3.86. Found: C, 52.77; H, 5.62; N, 3.82.

The resulting 4-(2,3-dimethoxyphenyl)-4-piperidinylmethanone trifluoroacetate was dissolved in water, treated with NaOH (10% aqueous) until basic, and extracted three times with dichloromethane. The combined organic layers were washed with brine, dried (MgSO$_4$), filtered, and evaporated to afford 4-(2,3-dimethoxyphenyl)-4-piperidinylmethanone as an oil.

E) (2,3-Dimethoxyphenyl)[1-[2-(4-fluorophenyl)ethyl]-4-piperidinyl]methanone monohydrochloride A solution of 4-(2,3-dimethoxyphenyl)-4-piperidinylmethanone (8.00 g, 32.1 mmol) and 2-(4-fluorophenyl)ethyl bromide (6.52 g, 32.1 mmol) was prepared in DMF (90 mL), treated with K$_2$CO$_3$ (7.0 g, 50.7 mmol), then stirred and heated at 80° C under argon overnight. The cooled solution was poured into a partition of 2/1 EtOAc/toluene and water. The layers were separated and the aqueous layer was extracted with 2/1 EtOAc/toluene. The combined organic layers were washed 2× with water, 1× with brine, dried (MgSO$_4$), filtered, and evaporated to afford 11.0 g of an oil. The oil was chromatographed on silica gel, eluting with EtOAc. The appropriate fractions were combined, concentrated, dissolved in ethyl acetate and treated with HCl/ethyl acetate. (2,3-dimethoxyphenyl)[1-[2-(4-fluorophenyl)ethyl]-4-piperidinyl]-methanone monohydrochloride was obtained as a precipitate, m.p. 225–227° C. (decomp). Anal Calcd for C$_{22}$H$_{26}$FNO$_3$·HCl: C, 64.78; H, 6.67; N, 3.43. Found: C, 64.44; H, 6.73; N, 3.41.

F) (+)-alpha-(2,3-Dimethoxyphenyl)-1-[2-(4-fluorophenyl)ethyl]-4-piperidinemethanol To a stirred solution of (2,3-dimethoxyphenyl)[1-[2-(4-fluorophenyl)ethyl]-4-piperidinyl]methanone (6.0 g, 16.2 mmol) in MeOH (100 mL) at 0° C. was added NaBH$_4$ (1240 mg, 32.8 mmol) in two portions, over a one hour period. After stirring overnight, the solution was concentrated to a solid. The solid was partitioned between water and ether. The layers were separated and the aqueous layer was extracted with ether. The combined organic layers were washed with brine, dried (MgSO$_4$), filtered, and evaporated to a solid. The solid was chromatographed on silica gel, eluting with acetone. The appropriate fractions were combined and evaporated to afford a white solid. The solid was recrystallized from cyclohexane to afford (±)-alpha-(2,3-dimethoxyphenyl)-1-[2-(4-fluorophenyl)-ethyl]-4-piperidinemethanol as white needles, m.p. 126–127° C.

Anal. Calcd for C$_{22}$H$_{28}$FNO$_3$: C, 70.75; H, 7.56; N, 3.75. Found: C, 70.86; H, 7.72; N, 3.93.

EXAMPLE 3

Starting Material

This example demonstrates the preparation of the alcohol, structure 5.

Preparation of (±)-alpha-(2,3-Dimethoxyphenyl)-1-[2-(4-fluorophenyl)ethyl]-4-piperidinemethanol A) Preparation of diastereomers.

A solution of 3.90 g (10.4 mmol) of (±)-alpha-(2,3-dimethoxyphenyl)-1-[2-(4-fluorophenyl)ethyl]-4-piperidinemethanol, 1.74 g (10.4 mmol) of S-(+)-alpha-methoxyphenylacetic acid, 2.15 g (10.4 mmol) of 1,3-dicyclohexylcarbodiimide and 0.1 g of 4-dimethylaminopyridine in chloroform (75 mL) was refluxed for 17 hours, allowed to cool to room temperature and filtered. The filtrate was concentrated and chromatographed on a silica gel column eluting with ethyl acetate/hexane (1:1) to afford two diastereomers, Rf=0.1 and 0.2 (TLC EtOAc/hexane, 1:1). Intermediate fractions were rechromatographed to give additional material. Those fractions with Rf=0.2 were combined to give a single diastereomeric ester, (+,+)-(2,3-dimethoxyphenyl)[1-[2-(4-fluorophenyl)ethyl]-4-piperidinyl]methyl-alpha-methoxybenzeneacetate.

B) Preparation of (+)-alpha-(2,3-Dimethoxyphenyl)-1-[2-(4-fluorophenyl)ethyl]-4-piperidinemethanol To a stirred solution of 0.97 g (1.9 mmol) of the above mentioned diastereomeric ester, Rf=0.2, in 25 mL of methanol was added 0.5 g (3.6 mmol) of potassium carbonate and 5.0 mL of water. After stirring 17 hours at room temperature the reaction mixture was diluted with water and extracted twice with methylene chloride,. The combined extracts were washed with water, brine and dried over MgSO$_4$. After filtering, the filtrate was concentrated to an oil and crystallized from 40 mL of cyclohexane/hexane (1:1) to give (+)-alpha-(2,3-dimethoxy-phenyl)-1-[2-(4-fluorophenyl)ethyl]-4-piperidinemethanol, m.p.112–113° C., $[\alpha]_D^{20}$=+13.9°.

EXAMPLE 4
(+)-α-(2,3-Dimethyoxyphenyl)-1-[2-(4-fluorophenyl)ethyl]-4-piperidinementhanol decanoate

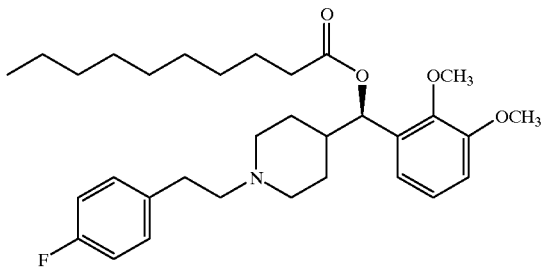

A mixture of 49.0 g (0.131 mol) of (+)-α-(2,3-dimethoxyphenyl)-1-[2-(4-fluorophenyl)ethyl]-4-piperidinemethanol, 500 mL of $CHCl_3$ and 16.0 g (0.158 mol) of triethylamine was charged into a one liter, 3-necked flask fitted with a stirrer, thermometer, dropping funnel, and a continuous nitrogen purge. A solution of 27.4 g (0.144 mol) of decanoyl chloride in 25 mL of $CHCl_3$ was added over 5 minutes while maintaining a reaction temperature of 20–25° C. The resulting solution was stirred at 20–25° C. for two hours. The progress of the reaction was monitored by TLC (5/95 methanol/$CH_2Cl_2$; Merck 60F-254 plates; UV; Rf of (+)-α-(2,3-dimethoxyphenyl)-1-[2-(4-fluorophenyl)ethyl]-4-piperidinemethanol—0.23; Rf of titled compound—0.55). An additional 2.8 g (0.015 mol) of decanoyl chloride (Aldrich) and 1.6 g (0.016 mol) of triethylamine was added to the reaction mixture and stirring was continued for two hours. The reaction mixture was diluted with 500 mL of $CH_2Cl_2$ and washed with 250 mL of 5% $K_2CO_3$, 250 mL of $H_2O$ and 250 mL of saturated NaCl. The organic phase was dried over 500 g of $MgSO_4$ and filtered. The filter lo cake was washed with 200 mL of $CH_2Cl_2$. The filtrate was concentrated at 400° C./50 torr to give an oil.

The crude product was purified by flash chromatography (14×29 cm column, 2.035 kg of 230–400 mesh silica gel). The crude product was loaded onto the column by dissolving it in 75 mL of $CH_2Cl_{2CH2Cl2}$. The column was eluted with 24 L of 1/4 EtOAc/$CH_2Cl_2$ collecting 24× one liter fractions. The fractions which were homogenous by TLC were combined and concentrated at 35° C./50 torr followed by 70° C./0.5 torr for one hour to give a colorless oil.

MS(M+=528)

Analysis: Calc. for $C_{32}H_{46}FNO_4$ (527.73): 72.83, %C; 8.79, %H; 2.65, %N. Found: 72.25, %C; 8.88, %H; 2.63, %N.

EXAMPLE 5
(+)-α-(2,3-Dimethoxyphenyl)-1-[2-(4-fluorophenyl)ethyl]-4-piperidinemethanol butyrate

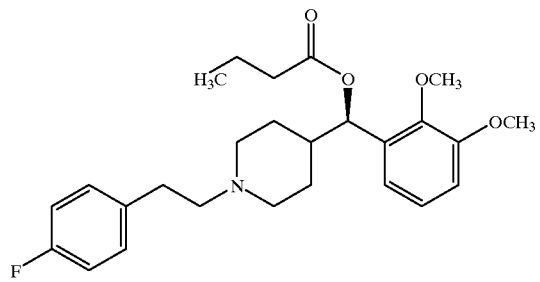

To a stirred solution of 2.0 g (5.37 mmol) of (+)-α-(2,3-dimethyloxyphenyl)-1-[2-(4-fluorophenyl)ethyl]-4-piperidinemethanol in 6 mL of dry methylene chloride was added 0.74 mL (0.537 g, 5.32 mmol) of triethylamine. The solution was cooled in an ice bath after which was added by syringe 0.96 mL (5.89 mmol) of butyric anhydride. The solution was stirred for several minutes at ice bath temperature and allowed to warm to room temperature. To the solution was then added 66 mg (0.541 mmol) of 4-dimethylaminopyridine. The mixture was stirred overnight at room temperature, poured into ice/water/0.5 M NaOH, extracted with ether, washed with water and saturated sodium chloride. The organic extract was dried ($Na_2SO_4$), filtered and concentrated to an oil. The oil was dissolved in methylene chloride and purified by flash chromatography on silica gel, eluting with methylene chloride, 1% and 2% methanol/methylene chloride, respectively. The pure product containing fractions were combined and concentrated to provide the tit ed compound. The compound was homogenous by TLC. IR (KBr), NMR ($CDCl_3$) and MS (MH+=445) were consistent with the proposed structure.

Analysis: Calc. for $C_{26}H_{34}FNO_4$: 70.40, %C; 7.73, %H; 3.16, %N. Found: 70.22, %C; 7.78, %H; 3.13, %N.

EXAMPLE 6
(+)-α-(2.3-Dimethoxyphenyl)-1-[2-(4-fluorophenyl)ethyl]-4-piperidinemethanol hexanoate

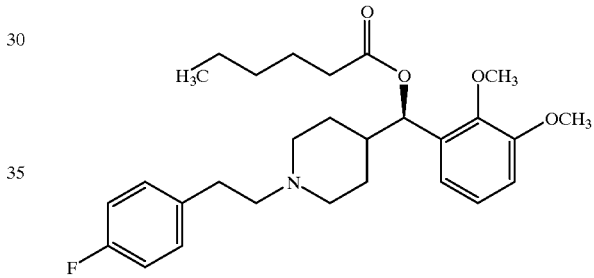

To a stirred solution of 2.0 g (5.37 mmol) of (+)-α-(2,3-dimethyloxyphenyl)-1-[2-(4-fluorophenyl)ethyl]-4-piperidinemethanol in 6 mL of dry methylene chloride was added 0.74 mL (0.537 g, 5.32 mmol) of triethylamine. The solution was cooled in an ice bath after which was added by syringe 1.07 mL (5.89 mmol) of hexanoic anhydride. The solution was stirred for several minutes at ice bath temperature and allowed to warm to room temperature. To the solution was then added 66 mg (0.541 mmol.) of 4-dimethylaminopyridine. The mixture was stirred overnight at room temperature, poured into ice/water/0.5 M NaOH, extracted with ether, and filtered and concentrated to an oil. The oil was dissolved in methylene chloride, and 2% methanol/methylene chloride, respectively. The pure product-containing fractions were combined and concentrated to provide an oil which was dried overnight at 60° C., under high vacuum to give the titled compound. The compound was homogenous by TLC. IR (Kbr), NMR ($CDCl_3$) and MS (MH+=472) were consistent with the proposed structure.

Analysis: Calc. for $C_{28}H_{38}FNO_4$: 71.31, %C; 8.12, %H; 2.97, %N. Found: 70.94, %; 8.07, %H; 2.88, %N.

EXAMPLE 7

(+)-α-(2,3-Dimethoxyphenyl)-1-[2-(4-fluorophenyl)ethyl]-4-piperidinemethanol octanoate

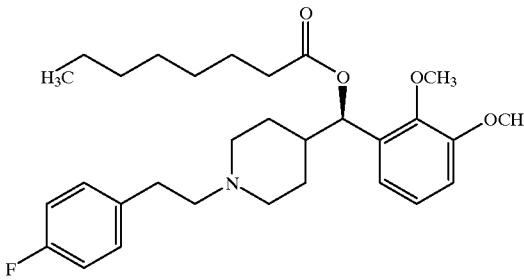

To a stirred solution of 2.0 g (5.37 mmol) of (+)-α-(2,3-dimethyloxyphenyl)-1-[2-(4-fluorophenyl)ethyl]-4-piperidinemethanol in 6 mL of dry methylene chloride was added 0.74 mL (0.537 g, 5.32 mmol) of triethylamine. The solution was cooled in an ice bath after which was added by syringe 1.75 mL (5.89 mmol) of octanoic anhydride. The solution was stirred for several minutes at ice bath temperature and allowed to warm to room temperature. To the solution was then added 66 mg (0.541 mmol) of 4-dimethylaminopyridine. The mixture was stirred, washed with water and saturated sodium chloride. The organic extract was dried ($Na_2SO_4$), filtered and concentrated to an oil. The oil was dissolved in methylene chloride and purified by flash chromatography on silica gel, eluting with methylene chloride, 1% and 2% methanol/methylene chloride, respectively. The pure product-containing fractions were combined and concentrated to provide an oil which was dried overnight at 60° C. under high vacuum to provide the titled compound. The compound was homogenous by TLC. The IR (KBr), NMR ($CDCl_3$) and MS (MH+=501) were consistent with the proposed structure.

Analysis: Calc. for $C_{30}H_{42}FNO_4$: 72.11, %C; 8.47, %H; 2.80, %N. Found: 71.94, %C; 8.63, %H; 2.83, %N.

EXAMPLE 8

(+)-γ-(2,3-Dimethoxyphenyl)-1-[2-(4-fluorophenyl)ethyl]-4-piperidinemethanol acetate

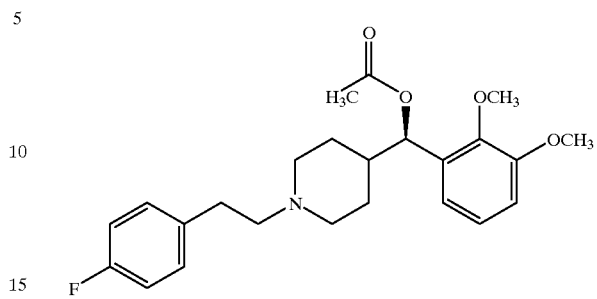

To a stirred solution of 2.00 g (5.36 mmol) of (+)-α-(2,3-dimethyloxyphenyl)-1-[2-(4-fluorophenyl)ethyl]-4-piperidinemethanol in 6 mL of dry methylene chloride was added 0.75 mL (5.38 mmol) of triethylamine via syringe after which the solution was chilled in an ice bath. To the solution was added 0.76 mL (8.06) mmol) of acetic anhydride after which the mixture was stirred at 0° C. for 15 minutes. The reaction mixture was allowed to warm to ambient temperature and to the reaction mixture was added 65 mg (0.536 mmol) of 4-dimethylaminopyridine after which the solution was stirred under nitrogen overnight. The reaction mixture was poured into 50 mL of 0.5 N sodium hydroxide and extracted twice with 50 mL of diethyl ether. The combined organic layers were washed with water and brine, dried over magnesium sulfate, filtered and concentrated to a yellow oil. The oil was dissolved in dichloromethane and purified using a flash chromatography column packed with silica gel and dichloromethane and eluted with the same solvent system followed by 0.5, 1.0, 1.5 and 2.0% methanol/methylene chloride, respectively. The appropriate fractions were combined and concentrated to a yellow oil. The oil was dried twice overnight at 60° C under high vacuum to provide the titled compound. The compound was homogenous by TLC. IR (film), NMR (CDCl3) and MS (MH+=416) were consistent with the proposed structure.

Analysis: Calc. for C24H30FNO4: 69.38, %C; 7.38, %H; 3.37, %N. Found: 69.14, %C; 7.16, %H; 3.33, %N.

EXAMPLE 9

(+)-α-(2,3-Dimethoxyphenyl)-1-[2-(4-fluorophenyl)ethyl]-4-piperidinemethanol hexadecanoate

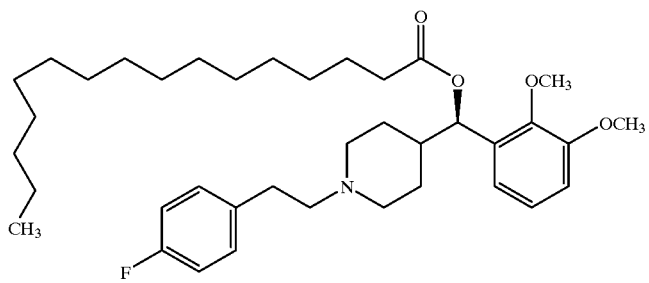

To a stirred solution of 2.00 g (5.36 mmol) of (+)-α-(2,3-dimethyloxyphenyl)-1-[2-(4-fluorophenyl)ethyl]-4-piperidinemethanol in 6 mL of dry methylene chloride was added 0.76 mL (5.46 mmol) of triethylamine via syringe after which the solution was chilled in an ice bath. To the solution was added 2.92 g (5.89) mmol) of hexadecanoic acid anhydride after which the mixture was stirred at 0C for 15 minutes. The reaction mixture was allowed to warm to ambient temperature and to the reaction mixture was added 65 mg (0.536 mmol) of 4-dimethylaminopyridine after which the solution was stirred under nitrogen overnight. The reaction mixture was poured into 50 mL of 0.5 N sodium hydroxide and 50 mL of diethyl ether. Some precipitate was observed and the resultant suspension was extracted with 1s methylene chloride. The methylene chloride layer was washed with water and brine, and dried over sodium sulfate, filtered, and concentrated to a yellow oil. The oil was dissolved in methylene chloride and purified using a flash chromatography column packed with silica gel and methylene chloride and eluted with the same solvent system followed by 1% and 2.0% methanol/methylene chloride, respectively. The appropriate fractions were combined and concentrated to a yellow oil. The oil was dried twice overnight at 60° C. under high vacuum to provide the titled compound. The compound was homogenous by TLC. IR (film), NMR (CDCl$_3$) and MS (MH+=612) were consistent with the proposed structure.

Analysis: Calc. for C$_{24}$H$_{30}$FNO$_4$: 74.59, %C; 9.55, %H; 2.29, %N. Found: 74.34, %C; 9.45, %H; 2.29, %N.

EXAMPLE 10
(+)-α-(2,3-Dimethoxyphenyl)-1-[2-(4-fluorophenyl)ethyl]-4-piperidinemethanol

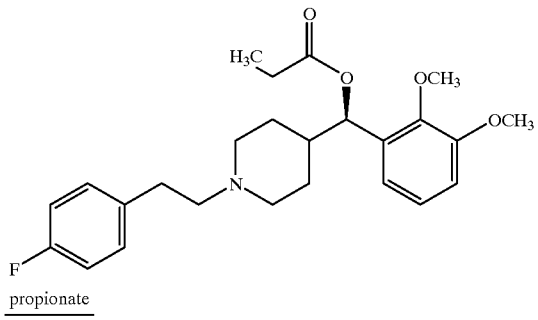
propionate

To a stirred solution of 1.80 g (4.82 mmol) of (+)-α-(2,3-dimethyloxyphenyl)-1-[2-(4-fluorophenyl)ethyl]-4-piperidinemethanol in 6 mL of dry methylene chloride was added 0.67 mL (4.81 mmol) of triethylamine via syringe after which the solution was chilled in an ice bath at 0° C. To the solution was added 0.68 mL (5.30 mmol) of propionic anhydride after which the mixture was stirred at 0° C. for 15 minutes. The reaction mixture was allowed to warm to ambient temperature and to the reaction mixture was added 58.9 mg (0.482 mmol) of 4-dimethylaminopyridine after which the solution was stirred under nitrogen overnight. The reaction mixture was poured into 50 mL of 0.5 N sodium hydroxide and extracted twice with 50 ml of diethyl ether. The combined organic layers were washed with water and brine, and dried over sodium sulfate, filtered, and concentrated to a yellow oil. The oil was dissolved in methylene chloride and purified using a flash chromatography column packed with silica gel and methylene chloride and eluted with the same solvent system followed by l% and 2% methanol/methylene chloride, respectively. The appropriate fractions were combined and concentrated to a orange oil. The oil was dried twice overnight at 60° C. under high vacuum to provide the titled compound. The compound was homogenous by TLC. IR (film), NMR (CDCl3) and MS (MH+=430) were consistent with the proposed structure.

Analysis: Calc. for C25H32FNO4: 69.91, %C; 751, %H; 3.26, %N. Found: 69.76, %C; 7.53, %H; 3.30, %N.

EXAMPLE 11
(+)-α-(2,3-Dimethoxyphenyl)-1-[2-(4-fluorophenyl)ethyl]-4-piperidinemethanol 2,2-dimethyloctanoate

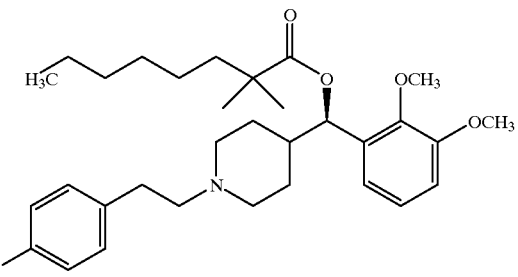

2-Hexene-1-mesylate is prepared by adding N,N-diisopropyl ethylamine (12.9 g, 0.1 m) to a solution of trans-2-hexene-1-ol (10.0 g, 0.1 m) (Aldrich) in 100 mL of methylene chloride. Methanesulfonyl chloride (12.6 g, 0.11 m) in methylene chloride (50 mL) is added dropwise to the solution with stirring at room temperature for 4 hours. The reaction mixture is transferred to a separatory funnel and washed with cold 1N HCl (2 times) and then with saturated NaHCO$_3$ solution (2 times). The solution is (tried over anhydrous MgSO$_4$, filtered and concentrated, under vacuum at 40° C. to give 2-hexene-1-mesylate.

2,2-Dimethyl-3-octene nitrile is prepared by adding 2-hexene-1-mesylate (11.02 g, 0.05 m) in anhydrous THF (100 mL) to a solution prepared by the addition of isobutyro nitrile (3.7 g, 0.053 m) in THF (25 mL) after treatment with NaH (60% in mineral oil)(2.1 g, 0.053 m) in dry THF (50 mL). The resulting reaction mixture is stirred at reflux for 5 hours, cooled and stirred with cold ethanol (95%) and concentrated under vacuum to remove solvents. After adding water (50 mL), the mixture is extracted with diethyl ether (3×40 mL). The extracts are washed with water and then saturated NaCl solution and dried over MgSO$_4$, filtered and concentrated to give 2,2-dimethyl-3-octene nitrile.

2,2-Dimethyl-3-octenoic acid is prepared by adding 2,2-dimethyl-3-octene nitrile (1.51 g, 0.01 m) to a solution prepared from 15% NaOH in butanol/H$_2$O (2:3) (30 mL). The reaction mixture is stirred and refluxed for 7 hours, is cooled and made acidic with 10% hydrochloric acid. The reaction mixture is extracted with diethyl ether and the extract washed with saturated NaCl and dried over MgSO$_4$, filtered and concentrated to give 2,2-dimethyl-3-octenoic acid.

2,2-Dimethyl octanoic acid is prepared by dissolving 2,2-dimethyl-3-octenoic acid (0.20 g, 1.1 mmol) in absolute ethanol blanketed with N$_2$ and 10% palladium on carbon which is then hydrogenated for 6 hours. The catalyst is removed by filtration and the filtrate concentrated under vacuum to give 2,2-dimethyl octanoic acid.

To a stirred solution of (+)-α-(2,3-dimethyloxyphenyl)-1-[2-(4-fluorophenyl)ethyl]-4-piperidinemethanol (3.9 g, 10.4 mmol) in 70 ml of methylene chloride is added dicyclohexylcarbodiimide (2.15 g, 10.4 mmol), 4-dimethylamino pyridine 0.1 g and 2,2-dimethyloctanoic acid (1.70 g, 10.4 mmol). The resulting solution is stirred and refluxed for 16 hours. The cooled reaction solution is filtered and concentrated to an oil The resulting oil is chromatographed on silica gel and eluted with ethyl acetate/hexane (1:1). Appropriate fractions are collected, warmed (40 C) and concentrated at reduced pressure to give the titled compound.

EXAMPLE 12

This example demonstrates one pharmaceutical composition of the present invention. In a suitable 100 mL volumetric vessel, place: 70 mL of Sesame Oil, NF (Sigma), 1.2 g of Benzyl Alcohol, NF and 14.129 g of (+)-α-(2,3-Dimethyoxyphenyl)-1-[2-(4-fluorophenyl)ethyl]-4-piperidinementhanol decanoate. To this solution add sufficient Sesame Oil, NF to bring the volume to 100 ml and mix until homogeneous. This solution may be sterilized and packaged for parenteral injection.

EXAMPLE 13

This example describes a behavioral test (antagonism of DOI-induced behaviors) designed to identify compounds which possess antagonist activity at the $5HT_{2A}$ receptor. The compound of the present invention used in this test was (+)-α-(2,3-Dimethyoxyphenyl)-1-[2-(4-fluorophenyl) ethyl]-4-piperidinemethanol decanoate—Example 4 herein. The 5-HT2A/2C agonist (±)-DOI HCl (1-(2,5-dimethoxy-4-iodophenyl)-2-aminopropane hydrochloride) induces several quantifiable behaviors in rats. These behaviors include "shakes" (a quick head and body shake, a.k.a. wet dog shakes), "forepaw tapping" (rapid forepaw treading) and "skin-jerks" (paraspinal muscle contractions or dorsal skin-shrugging). The 5-HT2 antagonists mianserin, ritanserin and methysergide as well as the selective 5-HT2A antagonist MDL 100,907 have been demonstrated to dose-dependently block the behavioral effects of DOI (Pranzatelli, 1990, *Neurosci. Let.* 11: 74–80; Wettstein et al., 1996, *Soc. Neurosci. Abs.* 22: 481). Significantly, drugs with $5-HT_{2A}$ antagonist activity have been proposed to have atypical antipsychotic properties in schizophrenic patients (Meltzer et al., 1989, *JPET.* 251: 238–246), as well as potential therapeutic activity in a number of other CNS disorders including depression, dysthymia, and anxiety (Stefanski & Goldberg, 1997, CNS Drugs, 7: 399–409)
Methods
Subjects and housing Male Sprague-Dawley rats (180±50 g) were housed seven per cage and allowed 1 week to acclimate to the vivarium. Food and water were freely available. The temperature and light cycle (12 h on-12 h off)were automatically maintained. Individual rats were tested once. Each testing group contained seven animals. Experiments took place in the vivarium room where the animals were housed.
Drug preparation and administration (+)-α-(2,3-Dimethyoxyphenyl)-1-[2-(4-fluorophenyl) ethyl]-4-piperidinemethanol decanoate (120 mg/kg equivalent to MDL 100,907) was dissolved in sesame oil and administered intramuscularly to separate groups of rats on Day 0 in a volume equal to 60 mL/100 g body weight. Vehicle control animals were injected with sesame oil alone. (±)-DOI HCl (3.0 mg/kg, 1 mL/kg body weight) was dissolved in distilled water with the aid an ultrasonic bath, and injected intraperitoneally on appropriate testing days.
Observation and behavioral assessment (+)-α-(2,3-Dimethyoxyphenyl)-1-[2-(4-fluorophenyl) ethyl]-4-piperidinemethanol decanoate-treated rats were tested for antagonism of DOI-induced behaviors 1, 5, 7, 14, 21, 28 and 40 days after the single (+)-α-(2,3-Dimethyoxyphenyl)-1-[2-(4-fluorophenyl)ethyl]-4-piperidinementhanol decanoate intramuscular injection. Each rat was tested once. Immediately after DOI injection rats were placed under inverted clear plastic boxes (28 L×25 W×25 H cm) which were arranged on top of clean absorbent paper. Rats were continuously watched by trained observers (blind to treatment) for 30 minutes for the occurrence of DOI-induced behaviors (shakes, skin-jerks and forepaw tapping bouts) and then returned to their home cages. Rats were later used for pharmacokinetic studies. The frequencies of DOI-induced behaviors were recorded and then summed to provide a single behavioral score for each animal.
Data Analysis The mean and standard error of the behavioral scores of each group was determined. Each treatment group's mean was then compared separately to the mean of the vehicle-control group using a one-way analysis of variance test (ANOVA), followed by a Bonferroni/Dunn post-hoc comparison. Differences between groups were considered statistically significant if p values were less than or equal to 0.05.
Results Significantly antagonized DOI-induced behavior in the rats was observed for a full 28 days. The effect was no longer significant at day 40.

EXAMPLE 14

This example demonstrates the single dose absorption of MDL 100,907 following intramuscular administration (i.m.) of (+)-α-(2,3-Dimethyoxyphenyl)-1-[2-(4-fluorophenyl) ethyl]- 4-piperidinemethanol decanoate, a compound of the present invention, over time.

A total of ninety male Wistar rats weighing approximately 150–200 grams each are dosed i.m. with (+)-α-(2,3-Dimethyoxyphenyl)-1-[2-(4-fluorophenyl)ethyl]-4-piperidinemethanol decanoate in sesame oil (equivalent to 120 mg/kg of MDL 100,907) on day 0. Rats are anesthetized with a lethal i.p. dose of nembutal and blood collected at 3 and 6 hours, and various days post-dose (n=5 for each timepoint) in heparinized vacutainers. Blood samples are centrifuged for 30 minutes at 5 C and at approximately 2700 rpm. Plasma is removed and stored at −20° C. until assay. The plasma samples are analyzed by an appropriate HPLC method. Brains will also be collected at the above timepoints and stored at −80° C. until analyzed by the appropriate HPLC method. The results are shown in Table 1.

TABLE 1

| Time (days) | (+)-α-(2,3-Dimethyoxyphenyl)-1-[2-(4-fluorophenyl)ethyl]-4-piperidinemethanol (ng/mL)- MDL 100,907 | (+)-α-(2,3-Dimethyoxyphenyl)-1-[2-(4-fluorophenyl)ethyl]-4 piperidinemethanol decanoate-Example 4 herein (ng/mL) |
|---|---|---|
| 0.125 | 21.48 ± 8.00 | 54.18 ± 13.33 |
| 0.25 | 24.30 ± 7.65 | 53.79 ± 17.13 |
| 1 | 32.00 ± 10.48 | 54.08 ± 17.98 |
| 2 | 25.59 ± 8.90 | 21.61 ± 7.39 |
| 3 | 25.48 ± 4.65 | 38.95 ± 5.64 |
| 4 | 31.82 ± 10.22 | 52.02 ± 12.92 |
| 6 | 32.84 ± 11.83 | 41.87 ± 14.64 |
| 8 | 34.93 ± 11.36 | 28.70 ± 9.16 |
| 12 | 19.89 ± 5.65 | 21.00 ± 12.79 |
| 15 | 11.67 ± 6.18 | 52.36 ± 15.20 |
| 19 | 6.37 ± 2.19 | 40.06 ± 8.44 |
| 22 | 15.93 ± 2.45 | 46.30 ± 9.31 |
| 26 | 15.51 ± 7.15 | 38.92 ± 9.35 |
| 29 | 13.22 ± 4.54 | 43.71 ± 10.81 |
| 41 | 9.88 ± 3.81 | 24.12 ± 9.15 |

The dosage range at which the compounds of Formula I exhibits their ability to block the effects of serotonin at the $5HT_{2A}$ receptor can vary depending upon the particular disease or condition being treated and its severity, the patient, the formulation, other underlying disease states that the patient is suffering from, and other medications that may be concurrently administered to the patient. Generally, the compounds of Formula I will exhibit their serotonin $5HT_{2A}$ antagonist properties at dosages of between about 0.001 mg/kg of patient body weight/day to about 100 mg/kg of patient body weight/day. The sustained release formulations may contain multiples of the foregoing dosages depending upon over what period the active ingredient is released. The dosage of the compounds of the present invention may be determined by administering the compound to an animal and determining the plasma level of the active ingredient.

The compounds of the present invention may be mixed with a pharmaceutically acceptable carrier capable of being administered by the preferred route in order to produce a sustained release of the compound of the present invention so that a therapeutically effective amount of the compound (+)-α-(2,3-Dimethoxyphenyl)-1-[2-(4-fluorophenyl)ethyl]-4-piperidinemethanol can be supplied to the patient over a period of days or weeks. Preferably the sustained release formulation comprises a compound of Formula I and a pharmaceutically acceptable carrier for parenteral administration as either an aqueous suspension, oil solution, oil suspension or emulsion. Some oils which may be used for intramuscular injection are sesame, olive, arachnis, maize, almond, cottonseed, peanut and castor oil, with sesame oil being preferred. A pharmaceutically acceptable preservative such as benzyl alcohol may also be added. The sustained release formulation is preferably administered intramuscularly or subcutaneously, with intramuscular administration preferred although other routes of administration such as oral, transdermal, nasal spray, etc. could be used if appropriate to the needs of the patient.

Since the compounds of the present invention release (+)-α-(2,3-Dimethoxyphenyl)-1-[2-(4-fluorophenyl)ethyl]-4-piperidinemethanol ("Active Ingredient") into the patient for the therapeutic effect, the compounds of the present invention are useful for all indications of use for which the Active Ingredient is useful. Some of these indications of use have been described in the patents issued generically encompassing the Active Ingredient (U.S. Pat. No. 4,783,471) or specifically covering the Active Ingredient (U.S. Pat. Nos. 5,134,149; 5,561,144; 5,618,824; and PCT/US97/02597), all incorporated herein by reference. These references disclose uses of psychosis (including schizophrenia), obsessive compulsive disorder, thrombotic illness, coronary vasospasm, intermittent claudication, anorexia nervosa, Raynaud's phenomenon, fibromyalgia, extra-pyramidal side effects, anxiety, arrhythmia, depression and bipolar depression, or drug abuse (e.g., cocaine, nicotine,etc.). Some of these indications have been disclosed in the patents described above and in U.S. Pat. Nos. 5,561,144; 5,618,824; 4,877,798; 5,134,149; and 5,021,428; all incorporated herein by reference.

Psychoses as used herein are a conditions where the patient experiences a major mental disorder of organic and/or emotional origin characterized by derangement of the personality and loss of contact with reality, often with delusions, hallucinations or illusions. Representative examples of psychotic illnesses which can be treated with the compounds of the present invention include schizophrenia, schizophreniform disorder, schizoaffective disorder, delusional disorder, brief psychotic disorder, shared psychotic disorder, psychotic disorder not otherwise specified, and substance-induced psychotic disorder. See Diagnostic and Statistical Manual of Mental Disorders, 4th ed., American Psychiatric Association, incorporated herein by reference. The Active Ingredient is currently in clinical trials for the treatment of schizophrenia.

Patients with obsessive-compulsive Disorders (OCD) fail to inhibit or "gate" intrusive, distressing thought or images. Since OCD is characterized by deficient "cognitive gating" and by aberrant metabolic activity in circuitry linking the orbital cortex and straitum, it has been predicted that OCD patients might exhibit deficient PPI (prepulse inhibition). The Active ingredient has been found to restore disrupted PPI. See Psychopharmacology 124: 107–116 (1996), R. A. Padich, et al., "5HT modulation of auditory and visual sensorimotor gating: II. Effects of $5HT_{2A}$ antagonist MDL 100,907 on disruption of sound and light preplulse inhibition produced by 5HT agonists in Wistar rats."

The Active Ingredient is also effective in the prevention of acute thrombosis, especially those of the coronary arteries. This compound decreases the rate at which platelets aggregate as the result of minor alterations in the endothelial lining of the vasculature and therefore prevent the formation of acute pathological thrombi. See U.S. Pat. No. 5,561,144 for description.

Anxiety, variant angina, anorexia nervosa, Raynaud's phenomenon and coronary vasospams are used in the manner defined in the 27th edition of Dorland's Illustrated Medical Dictionary, incorporated herein by reference.

Fibromyaligia is a chronic disease state wherein the patient suffers from numerous symptoms such as, for example, widespread generalized musculoskeletal pains, aching, fatigue, morning stiffness and a sleep disturbance which can be characterized as inadequacy of stage 4 sleep.

Extra-pyramidal side effects often accompany the administration of neuroleptic agents such as haloperidol and chlorpromazine. Patient often experiences a parkinsonian-like syndrome, wherein they experience muscular rigidity and tremors. Others experience akathisia and acute dystonic reactions.

The Active Ingredient increases the duration of the action potential of myocardial tissue producing an increase in the refractory period of that tissue, which under the classification system of Vaughan Williams, exhibits Class III anti-arrhythmic activity.

The compounds of the present invention may be used to treat drug abuse in the patient. See T. F. Meert, et al., European Journal of Pharmocology 183: 1924 where $5HT_2$ antagonist abolished preference for both alcohol and cocaine in the rodent model of the drug abuse. Other animal models such as the rodent self-stimulation model described in R. A. Frank, et. al., Behavioral Neuroscience 101: 546–559 1987) may be used to demonstrate the ability of the compounds of the p)resent invention to treat drug abuse.

The compounds of the present invention are useful in treating patients with Depressive Disorders and Bipolar Disorders. In the Diagnostic and Statistical Manual of Mental Disorders (Third Edition-Revised) ("DSM-III-R"), incorporated herein by reference, Depressive Disorders are defined as Major Depression, Dysthymia and Depressive Disorder NOS. We also include in this category Major Depressive Episode including Chronic Type, Melancholia, and Seasonal Pattern. Bipolar Disorders include Bipolar Disorder, Cyclothymia and Bipolar Disorder NOS.

A feature of Depressive Disorders is one or more periods of depression without a history of either Manic or Hypomanic episodes. A feature of Bipolar Disorders is the presence of one or more Manic or Hypomanic Episodes usually accompanied by one or more Major Depressive Episodes. A Manic or Hypomanic Episode is a distinct period during which the predominant mood is either elevated, expansive or irritable and there are associated symptoms of the Manic Syndrome as defined in DSM-III-R. The disturbance is severe enough to cause marked impairment in occupational or social functioning.

Major Depression has one or more Major Depressive Episodes. A Major Depressive Episode is characterized by: (1) at least five of the following) depressed mood, loss of interest in pleasure (anhedonia), significant weight loss or weight gain when not dieting, insomnia or hypersomnia, psychomotor agitation or retardation, fatigue or loss of energy, feelings of worthlessness or excessive or inappropriate guilt, diminished ability to think or concentrate, or recurrent thoughts of death including suicide; (2) it cannot be established that an organic factor initiated and maintained the disturbance; (3) there are no delusions or hallucinations for as long as two weeks in the absence of prominent mood symptoms; and (4) it is not superimposed on Schizophrenia, Schizophreniform Disorder, Delusional Disorder, or Psychotic Disorder NOS.

Dysthymia has a history of a depressed mood more days than not for at least two years and during the first two years of the disturbance, the condition does not meet the criteria for a Major Depressive Episode. The depressed mood in children and adolescents can be exhibited as irritability. Also present is at least two of the following: poor appetite or overeating, insomnia or hypersomnia, low energy or fatigue, low self-esteem, poor concentration or difficulty making decisions or feeling of hopelessness. These symptoms are not superimposed on a chronic psychotic disorder such as Schizophrenia or Delusional Disorder. Also it cannot be determined that an organic factor initiated and maintained the disturbance.

There are many ways to show that the compound of the present invention is useful in treating Depressive Disorders and Bipolar Disorders such as in animal models. See for example, "Animal Models as simulations of depression" by Paul Willner, *TiPS* 12:131–136 (April 1991); "Animal Models of Depression: An overview" by Paul Willner, *Pharmac. Ther.* 45:425–455 (1990), both of which are incorporated herein by reference. One such model is the Chronic Mild Stress Model of Depression ("CMS").

CMS uses mild stressors, such as food and water deprivation, small temperature changes, changes of cage mates, etc. Over a period of weeks of exposure to the mild stressors, the animals gradually reduce their consumption of a highly preferred sucrose solution which persists (in untreated animals) for several weeks following the cessation of stress. This decreased sensitivity to reward (the sucrose solution) reflects anhedonia, a symptom of a Major Depressive Episode (see for example, *Behavioral Pharmacol.*5: Suppl. 1, p. 86 (1994) where lithium, carbamazepine and ketoconazole were evaluated in CMS; *Psychopharmacology* 93:358–364 (1987) where a tricyclic antidepressant was evaluated in CMS; *Behavioral Pharmacology:*5:344–350 (1994) where a catechol-O-methyl transferase inhibitor was evaluated in CMS).

The following CMS study was performed using the Active Ingredient of the compounds of the present invention (hereafter "MDL 100,907") in comparison to known antidepressant compound Imipramine.

Male Wistar rats were brought into the laboratory two months before the start of the experiment at which time they weighed approximately 300 grams. Except as described below, the animals were singly housed, with food a water freely available, and maintained on a 12 hour light/dark cycle (lights on at 8 AM) at a temperature of 22±° C.

The animals were first trained to consume a 1% sucrose solution; training consisted of eight 1 hour baseline tests in which sucrose was presented, in the home cage, following 14 hours food and water deprivation; intake was measured by weighing pre-weighed bottles containing the sucrose solution at the end of the test. Subsequently, sucrose consumption was monitored, under similar conditions, at weekly intervals throughout the whole experiment.

On the basis of their sucrose intakes in the final baseline test, the animals were divided into two matched groups. One group of animals was subjected to a chronic mild stress procedure for a period of 9 consecutive weeks. Each week of stress regime consisted of: two periods of food or water deprivation (12 and 14 hour), two periods of 45 degree cage tilt (12 and 14 h), two periods of intermittent overnight illumination (lights on and off every 2 hours), two 14 hour periods of soiled cage (200 ml water in sawdust bedding), two 14 hour periods of paired housing, two 14 hour periods of low intensity stroboscopic illumination (150 flashes/min). Stressors were applied continuously throughout the day and night, and scheduled randomly. Control animals were housed in a separate room and had no contract with the stressed animals. They were deprived of food and water for the 14 hours preceding each sucrose test, but otherwise food and water were freely available in the home cage. On the basis of their sucrose intake scores following 3 weeks of stress, both stressed and control animals were each divided further into matched subgroups (n=8), and for subsequent five weeks they received daily administrations of vehicle (1 ml/kg, intraperineally (ip)) imipramine (10 mg/kg, ip) or MDL 100,907 (0.002, 0.02 and 0.2 mg/kg orally). All drug injections were in a volume of 1 ml/kg body weight. Drugs were administered at 10 AM and sucrose tests were carried out 24 hours following the last drug treatment. After five weeks, the treatments were terminated and after one week of withdrawal a final sucrose test was carried out. Stress was continued throughout the period of treatment and withdrawal.

Results were analyzed by multiple analysis of variance, followed by Fisher's LSD test for post hoc comparisons of means.

Chronic mild stress caused a gradual decrease in the consumption of 1% sucrose solution, in the final baseline test, sucrose intake was approximately 13 gram in both groups. Following three we a of stress (Week 0), intakes remained at 12.4 (±0.4) grams in controls but fell to 7.2 (±0.2) grams in stressed animals (p<0.001). Such a difference between control and stressed animals treated with vehicle, persisted at similar level for the remainder of the experiment.

Imipramine had no significant effect on the sucrose intake in control animals [F(1,84)=0.364; NS]. However, the drug caused a gradual increase of sucrose intake in stressed animals (F(1,84)=16.776; p<0.001]. Sucrose intake in imipramine-treated stressed animals was significantly increased from Week 0 scores after four weeks of treatment (p=0.05) and after five weeks of treatment there were no significant differences between drug-treated stressed animals and drug- and saline-treated controls. The increase of sucrose intake in imipramine-treated stressed animals was maintained at similar level one week after withdrawal from the drug.

MDL 100,907 had no significant effect on the sucrose intake in control animals [Treatment effect:F(3,168)=0.821; NS Treatment× Weeks interaction: F(15,168=0.499; NS]. In stressed animals, MDL 100,907 gradually reversed the CMS-induced deficit in sucrose intake, resulting in a significant Treatment effect [F(3,168)=22.567; p<0.001] and Treatment× Weeks interaction (F(15,158)=1.559; p=0.05].

In stressed animals treated with two higher doses of MDL 100,907 (0.02 and 0.2 mg/kg), sucrose intakes were significantly increased from initial scores (Week 0) after two (0.02 mg/kg) and three (0.2 mg/kg) weeks of treatment (p=0.03 and p=0.04, respectively). This effect was increased further during next weeks, and at the end of treatment period (Week 5) the amount of sucrose solution drunk by these animals was comparable to that of vehicle-treated controls and significantly higher than that of vehicle-treated stressed animals (0.02 mg/kg: p<0.001, 0.2 mg/kg: p-0.002).

At the lowest dose of 0.002 mg/kg., MDL 100,907 had no significant effect on the sucrose intake throughout the whole treatment period. In consequence, after five weeks of treatment the sucrose consumption of stressed animals treated with this dose did not differ from the intakes of the vehicle-treated stressed animals (p=0.860) and was significantly lower than the intakes of vehicle-treated controls (p<0.01). One week after withdrawal from the treatment, the sucrose intakes were not significantly changed in all of MDL 100,907-treated control (0.002 mg/kg:p=0.2, 0.02 mg/kg: p=0.9, 0.2 mg/kg: p=0.4) and stressed animals (0.002 mg/kg: p=0.6, 0.02 mg/kg: p=0.8, 0.2 mg/kg: p=0.6).

Of course, clinical trials on humans may also be used to show the usefulness of the compound of the present invention in treating depression such as using the Abbreviated Hamilton Psychiatric Rating Scale for Depression. This comprises a series of 17 categories in which the individual is rated, e.g., for depressed mood, guilt, suicide tendencies, insomnia, anxiety, etc., to reach a score which indicates to the clinician whether or not the patient is suffering depression.

What is claimed is:

1. A compound of Formula I:

FORMULA I

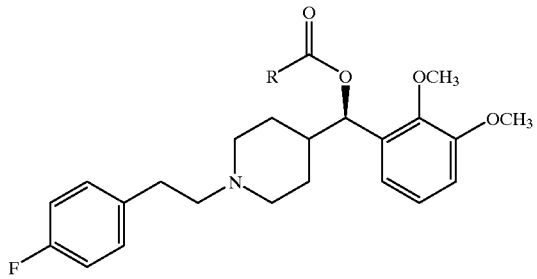

wherein R is $C_4–C_{20}$ alkyl, or a stereoisomer or a pharmaceutically acceptable salt thereof.

2. The compound of claim 1 wherein R is a straight chain alkyl.

3. The compound of claims 1 or 2 wherein R is $C_5–C_{20}$.
4. The compound of claims 1 or 2 wherein R is $C_5–C_{15}$.
5. The compound of claims 1 or 2 wherein R is $C_7–C_{15}$.
6. The compound of claims 1 or 2 wherein R is $C_7–C_9$.
7. The compound of claim 1 wherein the compound is (+)-α-(2,3-Dimethyoxyphenyl)-1-[2-(4-fluorophenyl)ethyl]-4-piperidinementhanol decanoate.
8. The compound of claim 1 wherein the compound is (+)-α-(2,3-Dimethoxyphenyl)-1-[2-(4-fluorophenyl)ethyl]-4-piperidinemethanol butyrate.
9. The compound of claim 1 wherein the compound is (+)-α-(2,3-Dimethoxyphenyl)-1-[2-(4-fluorophenyl)ethyl]-4-piperidinemethanol hexanoate.
10. The compound of claim 1 wherein the compound is (+)-α-(2,3-Dimethoxyphenyl)-1-[2-(4-fluorophenyl)ethyl]-4-piperidinemethanol octanoate.
11. The compound of claim 1 wherein the compound is (+)-α-(2,3-Dimethoxyphenyl)-1-[2-(4-fluorophenyl)ethyl]-4-piperidinemethanol hexadecanoate.
12. The compound of claim 1 wherein the compound is (+)-α-(2,3-Dimethoxyphenyl)-1-[2-(4-fluorophenyl)ethyl]-4-piperidinemethanol 2,2-dimethyloctanoate.
13. A method of treating a patient for psychoses comprising administering to the patient in need of such therapy a therapeutically effective amount of a compound according to claim 1.
14. The method of claim 13 wherein R is $C_9$ straight chain alkyl.
15. The method of claim 13 wherein the compound is administered by intramuscular or subcutaneous route.
16. The method of claim 13 wherein the compound is administered by intramuscular route, and the patient is treated from about 2 weeks to about one month.
17. A method of treating a patient for drug addiction comprising administering to the patient a therapeutically effective amount of a compound according to claim 1.
18. A pharmaceutical composition comprising the compound of the following Formula, or a stereoisomer or pharmaceutically acceptable salt thereof

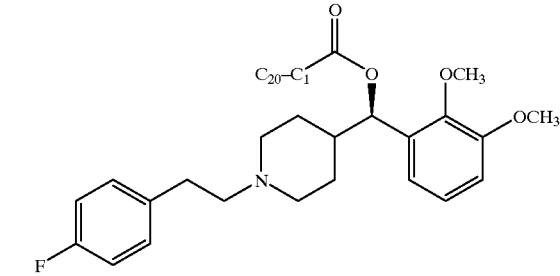

and a pharmaceutically acceptable carrier.

19. A method of making a compound of Formula I, a stereoisomer or pharmaceutically acceptable salt thereof, Formula I

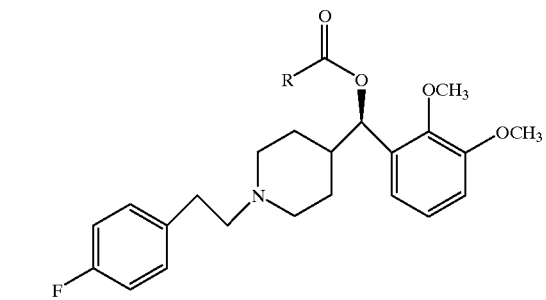

wherein R is $C_4–C_{20}$ alkyl
comprising reacting alcohol (5)

(5)

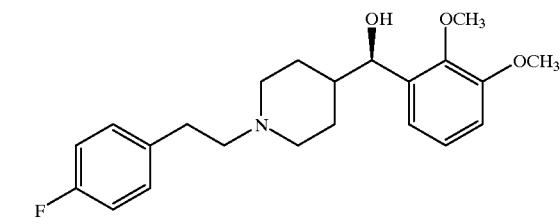

with an acid halide of the formula RC(O)X wherein X is a chloro or bromo, with R as previously defined, in the presence of a sufficient amount of an appropriate base to make the compound of Formula I.

20. The pharmaceutical composition of claim 18 wherein the R is C9 straight chain alkyl.
21. The pharmaceutical composition of claim 18 wherein the pharmaceutically acceptable carrier is a pharmaceutically acceptable oil.
22. The pharmaceutical composition of claim 21 wherein the oil is selected from the group consisting of sesame, olive, arachnis, maize, almond, cottonseed, peanut and castor oil.

23. The pharmaceutical composition of claim 22 wherein the oil is sesame oil.

24. The pharmaceutical composition of claim 18 wherein R is $C_9$ straight chain alkyl and the carrier is sesame oil.

25. A method for antagonizing the effects of serotonin at the $5HT_{2A}$ receptor comprising administering a therapeutically effective amount of a pharmaceutical composition according to claim 18 to a patient in need thereof.

26. The method of claim 21 wherein R is $C_9$ straight chain alkyl.

27. The method of claim 21 wherein the compound is administered by intramuscular or subcutaneous route.

28. The method of claim 26 wherein the compound is administered by intramuscular route, and the effects of serotonin at the $5HT_{2A}$ receptor are antagonized from about 2 weeks to about one month.

29. A method of treating a patient for depressive disorders comprising administering to the patient a therapeutically effective amount of a composition according to claim 18.

30. A method of treating a patient for anxiety comprising administering to the patient a therapeutically effective amount of a pharmaceutical composition according to claim 18.

31. A method of treating a patient for obsessive compulsive disorder comprising administering to the patient a therapeutically effective amount of a pharmaceutical composition according to claim 18.

32. A method of treating a patient for coronary vasospasms comprising administering to the patient a therapeutically effective amount of a pharmaceutical composition according to claim 18.

33. A method of treating a patient for angina comprising administering to the patient a therapeutically effective amount of a pharmaceutical composition according to claim 18.

34. A method of treating a patient for thrombotic illness comprising administering to the patient a therapeutically effective amount of a pharmaceutical composition according to claim 18.

35. The method of claim 19 wherein X is chloro.

36. The method of claim 19 wherein R is a straight chain alkyl.

37. The method of claim 19 wherein R is C5–C20.

38. The method of claim 19 wherein R is C7–C15.

39. The method of claim 19 wherein R is C7–C9.

40. The method of claim 19 wherein R is C9.

41. The method of claim 19 wherein the base is triethylamine.

42. The method of claim 19 wherein R is C9 and X is chloro.

43. A method of making a compound of Formula I, a stereoisomer or pharmaceutically acceptable salt thereof, wherein R is C4–C20 alkyl Formula I

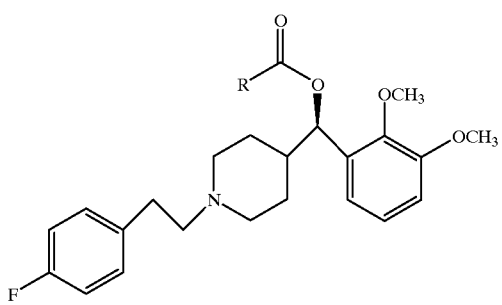

comprising reacting alcohol (5)

(5)

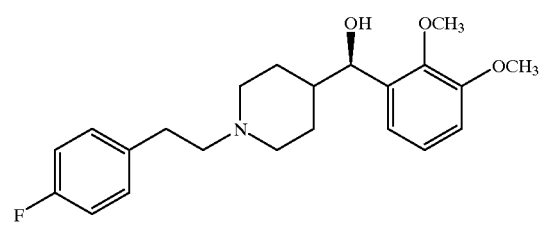

with an acid anhydride of the formula $(RCO)_2O$, wherein R is as previously defined, in the presence of a sufficient amount of an appropriate base to make the compound of Formula I.

44. The method of claim 43 wherein R is a straight chain alkyl.

45. The method of claim 43 wherein R is C5–C20.

46. The method of claim 43 wherein R is C7–C15.

47. The method of claim 43 wherein R is C7–C9.

48. The method of claim 43 wherein R is C9.

49. The method of claim 43 wherein the base is triethylamine.

50. The method of claim 43 wherein R is C9 and X is chloro.

51. A method of making a compound of Formula I, a stereoisomer or pharmaceutically acceptable salt thereof, Formula I

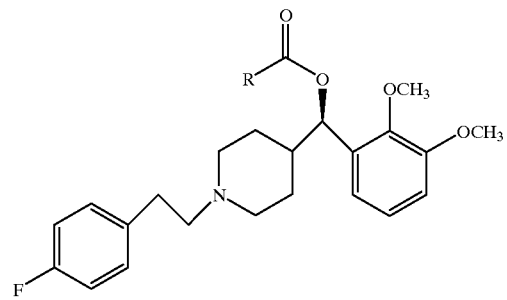

wherein R is C4–C20 alkyl comprising reacting alcohol (5)

(5)

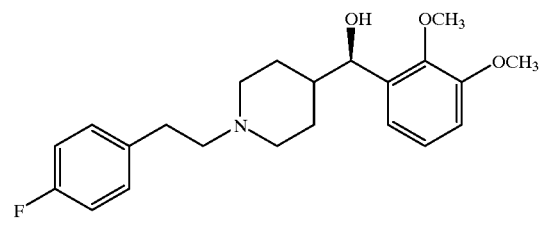

with the carboxylic acid of the formula $RCO_2H$, wherein R is as previously defined, in the presence of a sufficient amount of an appropriate base to make the compound of Formula I.

52. The method of claim 51 wherein R is a straight chain alkyl.

53. The method of claim 51 wherein R is C5–C20.

54. The method of claim 51 wherein R is C7–C15.

55. The method of claim 51 wherein R is C7–C9.

56. The method of claim 51 wherein R is C9.

57. The method of claim 51 wherein the base is triethylamine.

58. A method of treating a patient for bipolar depression comprising administering to the patient a therapeutically effective amount of a pharmaceutical composition according to claim 55.

* * * * *